US005685871A

United States Patent [19]

Lindholm-Ventola

[11] Patent Number: 5,685,871

[45] Date of Patent: Nov. 11, 1997

[54] APPARATUS FOR COLLECTING SEMEN

[75] Inventor: Jukka Lindholm-Ventola, Loimaa, Finland

[73] Assignee: Haico Oy, Loimaa, Finland

[21] Appl. No.: 596,342

[22] PCT Filed: Aug. 18, 1994

[86] PCT No.: PCT/FI94/00357

§ 371 Date: May 20, 1996

§ 102(e) Date: May 20, 1996

[87] PCT Pub. No.: WO95/05130

PCT Pub. Date: Feb. 23, 1995

[30] Foreign Application Priority Data

Aug. 18, 1993 [FI] Finland .................................... 933633

[51] Int. Cl.[6] ........................................ A61F 5/44

[52] U.S. Cl. ........................................ 604/349

[58] Field of Search ........................ 604/349, 330, 604/324, 317; 128/700, 767, 842–844; 119/14.5, 14.41, 14.44

[56] References Cited

U.S. PATENT DOCUMENTS

| | | | |
|---|---|---|---|
| 4,312,350 | 1/1982 | Doan | 604/349 |
| 4,690,678 | 9/1987 | Douglas-Hamilton | 604/349 |
| 4,744,352 | 5/1988 | Emery | 604/349 |
| 4,984,582 | 1/1991 | Romaniszyn et al. | 604/349 |
| 5,370,637 | 12/1994 | Brodeur | 604/329 |
| 5,437,652 | 8/1995 | Anatolievich | 604/349 |
| 5,540,670 | 7/1996 | Lindholm-Ventola | 604/349 |

FOREIGN PATENT DOCUMENTS

| | | |
|---|---|---|
| 1013596 | 7/1952 | France . |
| 2527924 | 12/1983 | France . |
| 2578414 | 9/1986 | France . |
| 2219813 | 11/1973 | Germany . |
| 85-109497/18 | 10/1984 | U.S.S.R. . |
| 86-188421/29 | 7/1985 | U.S.S.R. . |
| 0749041 | 5/1956 | United Kingdom . |

OTHER PUBLICATIONS

Lane Manufacturing Inc., "Colorado Model Equine Artificial Vagina", 1982.

*Primary Examiner*—John G. Weiss
*Assistant Examiner*—David J. Cho
*Attorney, Agent, or Firm*—Nixon & Vanderhye P.C.

[57] ABSTRACT

A collector funnel connected between an artificial vagina and a semen receiving unit, for animal breeding, has inner and outer jackets with an annular substantially gas-tight volume between the jackets. The inner jacket is made of resilient material and a partial vacuum is created in the annular volume to stretch the inner jacket so that it becomes smooth. The temperature within the annular volume may be regulated by intermittently or continuously passing a heating fluid at a temperature of greater than 30° C. through the annular volume, or by selectively operating electric heating elements disposed in the annular volume. The inner jacket may be disposable, i.e. replaced with a new inner jacket after one use. The annular volume between the jackets typically has a width of between about 5–10 mm.

20 Claims, 2 Drawing Sheets

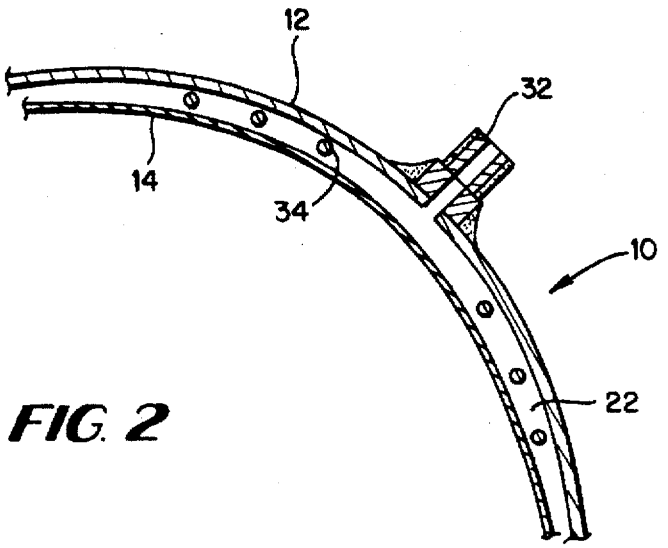
FIG. 2
FIG. 3
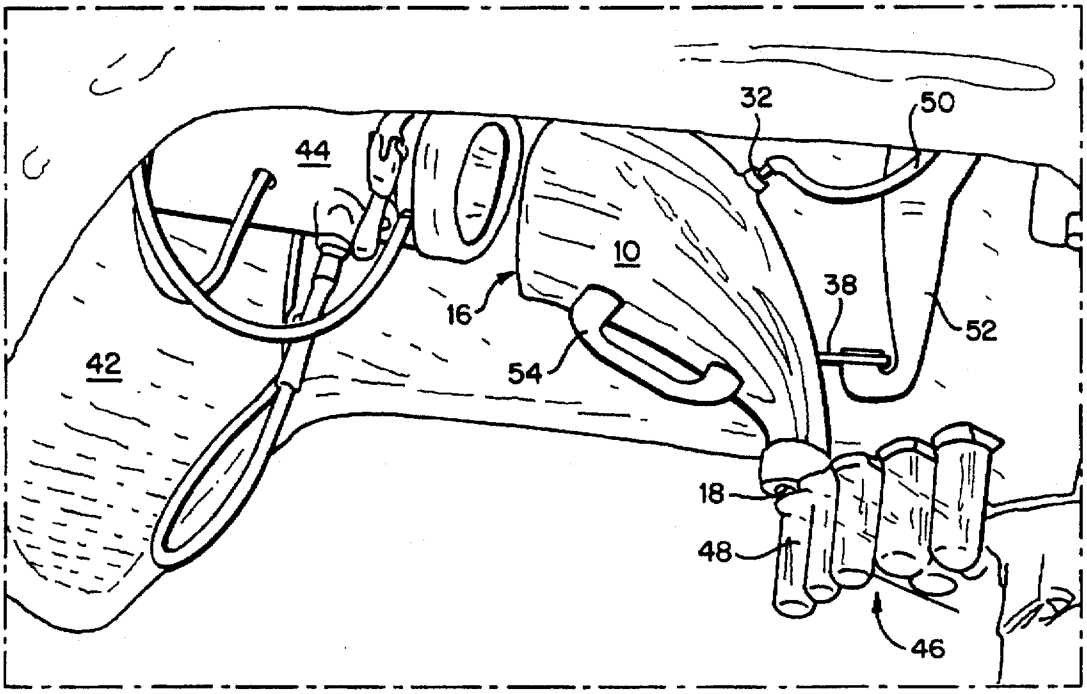

APPARATUS FOR COLLECTING SEMEN

CROSS-REFERENCE TO RELATED APPLICATION

This is a U.S. National Phase of PCT/FI94/00357 filed Aug. 18, 1994.

BACKGROUND AND SUMMARY OF THE INVENTION

The invention relates to an apparatus for collecting semen to be used in animal breeding, which apparatus comprises a collector funnel curving mainly downwardly from the horizontal to the vertical and at the same time narrowing, the apparatus having a semen-receiving opening at its upper end and a discharge opening for the semen at its lower end. The collector funnel can be fitted between an artificial vagina and a semen-receiving unit so as to conduct the semen passing through the artificial vagina to the receiving unit.

It is known from horse breeding studies that the stallion ejaculates in pulses and that the first fractions of the semen contain sperms and the rest only seminal plasma. In modern animal breeding, therefore, the so called open method is used for collecting semen, in which from the semen discharged during the ejaculation only the fractions having a high content of sperms are collected. The collecting of semen is performed by means of an artificial vagina attached to a dummy horse. From the artificial vagina the semen fractions are conducted, for instance by means of an ordinary funnel, to receivers or bags for the various fractions.

The semen collected by the open method is as such microbiologically and bacteriologically clean, and no screening or centrifuging is needed, if the right fraction of the semen is collected. Treatment of the semen, which is sensitive to light and air, for separating a good fraction from a fraction which has been badly collected would not be advantageous as regards the final result.

When collecting semen during the forceful ejaculation, some of the semen may splash out of the funnel and some of it will adhere to the walls of the funnel and does not flow into the receivers as desired. Thus, the best part of the semen as regards the artificial insemination may not be collected or can flow into the wrong receiver.

A further disadvantage of the open method of collecting semen is that some of the collected semen will already be destroyed in the initial phase when the sperms impinge with great force on the wall of the funnel. It has been proven by studies that the cellular structure of the sperms have been damaged, which directly influences the genome.

Another problem as regards keeping the semen fit for artificial insemination is caused by the fact that the sperms-containing semen having a temperature of 37° C. hits the inner surface of the funnel having a much lower temperature. The temperature difference may be more than 20° C., which results in a so called cold shock phenomenon. Due to this the metabolism of the sperms decrease, the swimming pattern changes and above all their mobility diminishes.

Besides the temperature difference between the semen and the funnel there may be areas having different temperatures in the funnel, which results in the fact that the viscosity of the semen varies at various points of the funnel and the flow of the semen from the funnel into the receiver may in some parts be retarded. The poorest semen, which has been discharged at the end of the ejaculation and does not contain any sperms, may then overtake semen of the best quality, which has been discharged earlier, whereby the sequence of the fractions flowing down changes and the received fractions do not fulfill the requirements as regards the content of sperms.

It is an object of the present invention to provide an apparatus in which the problems mentioned above are minimized.

It is a specific object to provide an apparatus by means of which the best fractions of the semen can be collected reliably and as well as possible, without weakening the quality of the semen.

The above objects of the inventions are attained by an apparatus according to the invention having the characteristic features set forth in the appended claims.

By means of the apparatus according to the invention, the semen of the animal is collected so that the ejaculated semen can be sorted according to quality more accurately than previously into separate receivers, and that the quality and preservability are good, due to being collected faster than previously.

In the arrangement according to the invention, the collector funnel comprises an outer jacket and an inner jacket of substantially the same shape as the outer jacket but having a smaller diameter, made of a resilient material. The inner jacket can be disposed, preferably concentrically, in the outer jacket so that a ring-shaped, substantially tight space is formed between the jackets. The collector funnel further comprises means for bringing about a vacuum in the space between the jackets so as to smooth the inner jacket by stretching it towards the outer jacket. The semen can then flow freely downwards in the funnel.

The gap between the inner and the outer jacket when the inner jacket is stretched is preferably about 5–10 mm. This gap forms an impact damper in the funnel, the inner jacket nevertheless remaining smooth-faced. The pressure brought about in the space between the jackets is preferably adjustable.

Connections for conducting a heating medium, a liquid or a gas such as air, having a temperature of 20°–40° C., preferably >30° C., intermittently or continually through the space between the jackets, can additionally be arranged in the funnel. Alternatively, electric heating elements can be fitted into the space between the jackets to heat the space or the medium in the same to a desired temperature.

The respective cross sections of the upper and lower ends of the inner jacket and the outer jacket of the collector funnel are preferably substantially the same size, the length of the inner jacket being slightly greater. The edges of the upper and lower ends can then be bent over the edges of the outer jacket for attaching the inner jacket to the outer jacket. The inner jacket is thus attached at its ends to the outer jacket tube.

The collector funnel can be fitted into a dummy horse or the like so that the semen coming from the artificial vagina to the collector funnel primarily hits the larger curved back wall of the funnel, from where the liquid further flows along the downwards sloping part of the back wall.

The outer as well as the inner jackets are shaped like a tube narrowing at one end and widening at the other end. The outer jacket is preferably made of a material firmly retaining its shape, such as stainless steel. The inner jacket is made of a resilient material, such as plastics, rubber, a rubber mixture or the like. The inner jacket may be such as to be disposed of after being used only once or to be changed after having been used a number of times.

The inner surface of the collector funnel according to the invention forms a resilient impact surface for the semen. By means of the resilient impact surface, the impact against the inner surface of the collector funnel of the sperms discharged during the ejaculation is dampened. On the other hand, the cold shock phenomenon of the sperms is prevented by means of the heatable inner part of the collector funnel. By using the collector funnel according to the invention it is thus possible to keep the conditions for collecting semen nearly natural. The viscosity and the flow velocity of the semen remain ideal.

The invention is described with reference to an exemplary embodiment thereof illustrated in the accompanying drawings, wherein:

BRIEF DESCRIPTION OF THE DRAWINGS

FIG. 2 is a partial cross-sectional view taken on the line A—A of FIG. 1; and

FIG. 3 is a schematic view of the collector funnel of FIG. 1 fitted into the lower part of the body of a dummy horse.

DETAILED DESCRIPTION OF THE DRAWINGS

Figure 1:
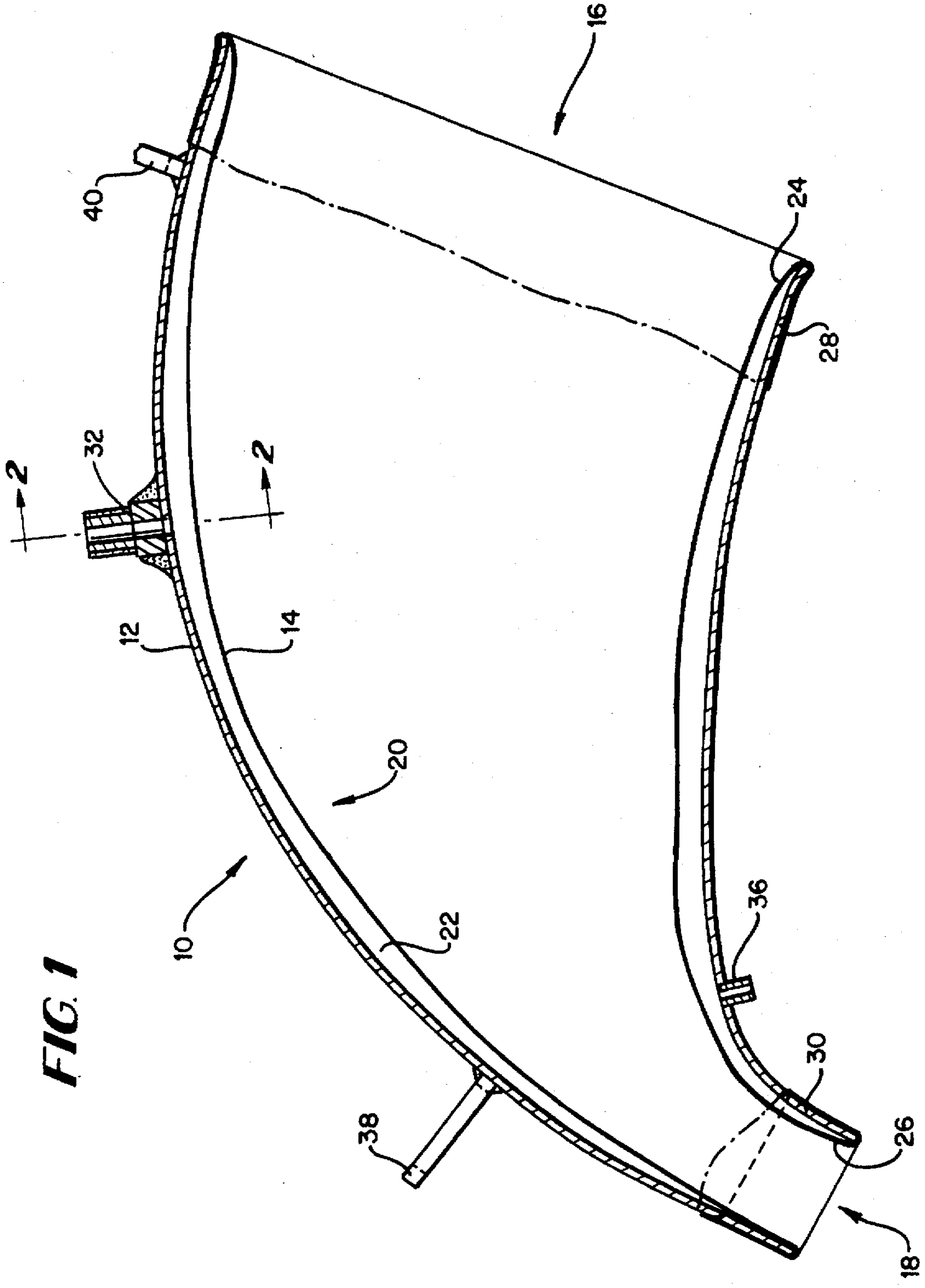
FIG. 1 is a schematic, elevational view in section of a collector funnel according to the invention.

FIG. 1 shows a vertical section of a collector funnel 10 according to the invention. An outer tubular jacket 12 made of metal, for instance stainless steel, and an inner tubular jacket 14 made of resilient material form the body of the collector funnel 10. The diameter of the cross section of the inner jacket 14 at the middle of the collector funnel is smaller than the diameter of the corresponding cross section of the outer jacket 12.

There is a semen-receiving opening 16 directed mainly sidewards, at one end of the collector funnel, and a discharge opening 18 directed mainly downwards at the other end. The receiving opening 16 has a larger cross-sectional area than the discharge opening 18. The collector funnel can be said to be shaped like a downwardly curved horn, in which the gently downwards curving upper part forms the back wall 20 of the collector funnel. The back wall 20 is curved from the receiving opening 16 to the discharge opening 18 at an angle of about 90°.

A tight intermediate space 22 is formed between the outer jacket 12 and the inner jacket 14 of the collector funnel 10 by bending the edges 24 and 26 of the inner jacket over the edges 28 and 30 of the outer jacket. The edges of the inner jacket are attached to the surface of the outer jacket, for instance by means of a rubber band. The inner jacket is made of a resilient material, such as PVC, rubber, a rubber mixture or the like. The inner jacket is easily changeable and forms thus at the same time a hygienic protective film.

The space 22 between the jackets can preferably be filled with a heating medium or other medium so as to keep the inner jacket 14 suitably warm and elastic. A connection 32 for feeding a heating medium, such as air, other gas, water or other liquid, into the space 22 between the jackets or away from it, is arranged through the outer jacket. The purpose of the inner jacket of the collector funnel is in particular to form a soft resilient surface at least at the back wall of the funnel. The connection 32 is therefore connected to an air pump or some other pump and valve combination (not shown) for bringing about a vacuum in the intermediate space 22. By a suitable vacuum in the intermediate space 22, the inner jacket 14 can be stretched towards the outer jacket 12 so that the inner surface of the inner jacket is free of wrinkles and the semen will not stick to the inner surface. However, the vacuum has to be regulated to a level at which the inner surface of the jacket retains its elasticity.

The inner and the outer jacket are preferably dimensioned so that a heating layer having a thickness of about 5–10 mm can be formed in the space 22 between the jackets. The vacuum required is dependent on the material of the inner jacket 14.

FIG. 2 shows a portion of a cross section through the collector funnel, taken along the line A—A of FIG. 1. Electric heating elements 34 are disposed between the jackets 12 and 14 at the inner surface of the outer jacket for heating the heating layer to a suitable temperature. The heating elements can alternatively, if desired, be attached on the outer surface of the metallic outer jacket 12, whereby the heated outer jacket transfers heat to the heating medium so as to heat the inner jacket.

If desired, the collector funnel can alternatively be heated by a continuous flow-through of a preheated heating medium in the intermediate space 22. A connection 36 (FIG. 1) having a substantially smaller diameter than the connection 32 is for this purpose disposed in the lower part of the upper jacket to continually feed a preheated medium into the intermediate space 22. Heating medium is continually withdrawn from the intermediate space by means of the connection 32. Several connections 36 may be provided, for instance arranged in a ring around the lower part of the collector funnel, for feeding heating medium into the intermediate space 22. Several connections 32 may also be provided for withdrawing heating medium from the intermediate space. The heating can in this way be made more efficient and more rapid and a funnel the temperature of which is more even and easier to control can be provided. For heating the collector funnel, the same medium which is used for heating the artificial vagina can be used. The collector funnel 10 is locked to the body of the dummy horse by means of brackets 38 and 40 to a separate mounting frame in the dummy horse.

The back wall 20 of the collector funnel 10 receives the ejaculated semen, the movement and impact of which is retarded and dampened by the resilient impact surface formed by the inner jacket of the funnel. The shape and the smoothness of the back wall prevents turbulent flow from developing and conduct the semen substantially as a laminar flow downwards toward the discharge opening 18 and out through the same. Turbulent flow at the discharge opening would cause harmful accumulation of semen around the opening. The collector funnel 10 is designed so that horizontal portions, in which semen could accumulate, are carefully avoided.

The cold shock phenomenon to the sperms is avoided by means of the heatable inner jacket 14, because the sperms are brought into contact with a warm dampening surface in the collector funnel. The temperature of the heating medium in the intermediate space 22 and thus also that of the inner jacket tube 14 is preferably kept between 20°–40° C., mainly however >30° C., which studies have proved to be sufficient. As it has been possibly to maintain nearly natural conditions during the collecting of the semen, the sperms retain their mobility and viability, and the viscosity and the flow velocity of the semen remain at the same time nearly ideal during the journey towards the receiver unit where it is finally collected.

FIG. 3 shows the position of the collector funnel 10 according to the invention in the body 42 of the dummy horse. The collector funnel 10 is fitted into the body of the dummy horse covered by a resilient material, between an artificial vagina 44 and a receiver unit 46. The distance of the collector funnel 10, provided with an upper semen-receiving opening 16 and a lower discharge opening 18 which is directed mainly downwards, can be adjusted steplessly between 0–150 mm in relation to the artificial vagina. All semen released during the ejaculation is collected in stages through the collector funnel 10 into separate receivers 48.

The heat medium which is used is supplied and/or withdrawn, and the pressure in the space between the outer and inner jacket of the collector funnel 10 is regulated through the connection 32 attached to the collector funnel 10. The connection 32 is connected by means of a hose 50 to an air pump or a pump and valve combination. The collector funnel 10 is locked to a separate adjustable mounting frame 52 in the body 42 of the dummy horse. The collector funnel 10 can easily be detached by means of a handle 54 fastened to it through the open stomach part of the dummy horse for cleaning and sterilization.

It is obvious to a person skilled in the art that various embodiments of the invention can vary within the scope of the appended claims.

I claim:

1. A collector funnel for conducting semen from an artificial vagina to a semen-receiving unit, comprising:

a body having an upper end and a lower end, and curving primarily downwardly from said upper end to said lower end while simultaneously narrowing;

a first, semen receiving opening at said upper end having a first cross-sectional area;

a second, discharge opening at said lower end, said discharge opening having a second cross-sectional area smaller than said first cross-sectional area;

said body comprising an outer jacket and an inner jacket of substantially the same shape as said outer jacket but having a smaller cross-sectional area, both said inner and outer jackets extending substantially between said first and second openings;

said inner jacket made of a resilient material and disposed within said outer jacket to define an annular substantially gas-tight volume between said inner and outer jackets; and means for evacuating air from said substantially gas-tight volume to provide a partial vacuum in said volume between said jackets so as to maintain said inner jacket resilient material substantially smooth by stretching it toward said outer jacket.

2. The apparatus as recited in claim 1 further comprising:

an artificial vagina connected to said first opening, for supplying semen to said collector funnel; and a semen-receiving unit connected to said second opening for receiving semen from said collector funnel.

3. The apparatus as recited in claim 2 where said collector funnel body includes a large curved backwall; and is connected to said artificial vagina so that semen passing from said artificial vagina to said collector funnel primarily impinges on said large curved backwall of said funnel body and is then directed obliquely downwardly from the point of impingement toward said second opening.

4. The apparatus as recited in claim 2 further comprising electric heating elements disposed in said annular volume to heat fluid within said annular volume.

5. The apparatus as recited in claim 2 further comprising first and second connections in said outer jacket for passing a heating medium having a temperature of greater than 30° C. through said annular substantially gas-tight volume.

6. The apparatus as recited in claim 2 wherein said annular substantially gas-tight space, when said inner jacket is stretched smooth by said evacuating means, has a width of between about 5–10 mm.

7. The apparatus as recited in claim 1 wherein said annular substantially gas-tight volume, when said inner jacket is stretched smooth by said evacuating means, has a width of between about 5–10 mm.

8. The apparatus as recited in claim 1 further comprising first and second connections in said outer jacket for passing a heating medium having a temperature of greater than 30° C. through said annular substantially gas-tight volume.

9. The apparatus as recited in claim 8 further comprising means for intermittently circulating the heating medium between said connections.

10. The apparatus as recited in claim 8 further comprising means for continuously circulating the heating medium between said connections.

11. The apparatus as recited in claim 1 wherein said inner and outer jackets each have upper and lower ends; and wherein said inner jacket has a slightly longer length than said outer jacket; and further comprising edge portions of said inner jacket at said upper and lower ends thereof bent over edges of said upper and lower ends of said outer jacket for attaching said inner jacket to said outer jacket.

12. The apparatus as recited in claim 1 wherein each of said inner and outer jackets are shaped like a tube which narrows at a first end and widens at a second end.

13. The apparatus as recited in claim 1 wherein said inner jacket is made of resilient plastic, rubber, or a rubber mixture.

14. The apparatus as recited in claim 13 wherein said outer jacket is rigid.

15. The apparatus as recited in claim 1 wherein said inner jacket is constructed so as to be disposed of after a single use.

16. The apparatus as recited in claim 1 further comprising electric heating elements disposed in said annular volume to heat fluid within said annular volume.

17. The apparatus as recited in claim 16 further comprising first and second connections in said outer jacket for passing a heating medium having a temperature of greater than 30° C. through said annular substantially gas-tight volume.

18. The apparatus as recited in claim 17 wherein said annular substantially gas-tight space, when said inner jacket is stretched smooth by said evacuating means, has a width of between about 5–10 mm.

19. The apparatus as recited in claim 1 whereins said outer jacket is rigid.

20. The apparatus as recited in claim 19 wherein said outer jacket is made of stainless steel.

* * * * *